United States Patent
Hayashi et al.

(10) Patent No.: US 8,021,495 B2
(45) Date of Patent: Sep. 20, 2011

(54) PIPETTE CLEANING DEVICE AND CLEANING METHOD

(75) Inventors: Masayoshi Hayashi, Amagasaki (JP);
Kazuhito Tanimoto, Amagasaki (JP);
Keiko Sasaki, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 342 days.

(21) Appl. No.: 11/918,797

(22) PCT Filed: Apr. 21, 2006

(86) PCT No.: PCT/JP2006/308390
§ 371 (c)(1),
(2), (4) Date: Oct. 17, 2007

(87) PCT Pub. No.: WO2006/115189
PCT Pub. Date: Nov. 2, 2006

(65) Prior Publication Data
US 2009/0114250 A1  May 7, 2009

(30) Foreign Application Priority Data
Apr. 21, 2005  (JP) .................................. 2005-123179

(51) Int. Cl.
*B08B 9/023* (2006.01)
*B08B 9/032* (2006.01)
*B08B 3/04* (2006.01)

(52) U.S. Cl. .... 134/34; 134/170; 134/166 C; 134/22.12; 15/104.04; 15/104.05

(58) Field of Classification Search ..................... 134/34, 134/170, 182, 166 C; 15/104.04, 104.05
See application file for complete search history.

(56) References Cited

U.S. PATENT DOCUMENTS

| | | | |
|---|---|---|---|
| 4,989,623 A | 2/1991 | Hoffman et al. | |
| 5,066,336 A | 11/1991 | Hoffman et al. | |
| 5,133,373 A * | 7/1992 | Hoffman et al. | 134/88 |
| 5,443,791 A | 8/1995 | Cathcart et al. | |
| 5,896,879 A * | 4/1999 | Gross et al. | 134/182 |
| 6,422,248 B1 * | 7/2002 | Furst et al. | 134/22.11 |
| 2003/0156282 A1 | 8/2003 | Komatani et al. | |

FOREIGN PATENT DOCUMENTS

| | | |
|---|---|---|
| DE | 196 17 206 | 11/1997 |
| EP | 0 503 003 | 9/1995 |
| EP | 0 816 853 | 1/1998 |
| JP | 58-163870 | 9/1983 |
| JP | 60-131862 | 7/1985 |
| JP | 5-502726 | 5/1993 |

(Continued)

*Primary Examiner* — Michael Kornakov
*Assistant Examiner* — Natasha Campbell
(74) *Attorney, Agent, or Firm* — Jordan and Hamburg LLP

(57) ABSTRACT

Provided are a simple and inexpensive cleaning apparatus and a method for cleaning capable of effectively cleaning the outer wall surface of a pipette. A pipette to be cleaned is positioned in a concave portion of the cleaning apparatus, and a cleaning liquid passed through inside of the pipette strikes an inner circumferential surface of the concave portion and bounces therefrom to splash against the outer wall surface of the pipette, thereby cleaning the outer surface. With above arrangement, without using an ejection apparatus of cleaning water, effect equivalent to that with the ejection apparatus can be attained. Furthermore, both the inner wall surface and the outer wall surface of the pipette can be cleaned by a single operation using the same cleaning water, thereby attaining easy internal cleaning work and short cleaning time.

19 Claims, 6 Drawing Sheets

FOREIGN PATENT DOCUMENTS

| | | |
|---|---|---|
| JP | 10-71339 | 3/1998 |
| JP | 2001-337094 | 12/2001 |
| JP | 2003-240787 | 8/2003 |
| JP | 2003240787 * | 8/2003 |
| JP | 2003-270235 | 9/2003 |
| WO | WO-91/08061 | 6/1991 |
| WO | WO-91/16675 | 10/1991 |

\* cited by examiner

PIPETTE CLEANING DEVICE AND CLEANING METHOD

BACKGROUND OF THE INVENTION

The present invention relates to a pipette cleaning apparatus and a method for cleaning the pipette, applied mainly to a dispenser of an autoanalyzer, and relates specifically to a cleaning apparatus and a cleaning method for cleaning the pipette, which clean the outer wall surface of the pipette using a cleaning liquid that once cleaned inside of the pipette.

A dispensing pipette in an autoanalyzer sucks to collect a dispensing liquid such as a testing sample and a reagent solution by immersing the pipette therein, and then dispenses the collected dispensing liquid in a vessel. Through the procedure, the inner wall surface and the outer wall surface of the pipette are contaminated by the dispensing liquid. Accordingly, the inner wall surface thereof is cleaned by letting a pure water to introduce into the pipette and to pass therethrough, while the outer wall surface thereof is cleaned by letting a pure water eject from outside of the pipette against the outer wall thereof. That is, the inner wall surface and the outer wall surface of the pipette are separately cleaned using the respective separate pure waters.

SUMMARY OF THE INVENTION

Installing a mechanism of ejecting pure water against the outer wall surface of a pipette has, however, drawbacks of increased size and increased cost of apparatus.

The present invention has been perfected to solve the problems, and an object of the present invention is to provide a simple and inexpensive cleaning apparatus and a cleaning method capable of effectively cleaning the outer wall surface of a pipette.

To achieve the object, the inventors of the present invention, as a result of detailed studies, came to think that the cleaning water which was once used to clean the inner wall surface of the pipette can be reused to perform dynamic cleaning, and found that there can be eliminated a special apparatus for ejecting the cleaning water by letting the cleaning water hit on the inner circumferential surface of a concave portion and letting the hit cleaning water bounce therefrom to splash to perform cleaning, which attains equivalent effect of the cleaning to that of ejection of cleaning water, thereby perfecting the present invention.

In concrete terms, according to the present invention, a pipette as a subject to be cleaned is positioned in a concave portion, and a cleaning liquid passed through inside of the pipette is brought to hit on the inner circumferential surface of the concave portion and to bounce therefrom to splash against the outer wall surface of the pipette, thus cleaning the outer wall surface.

The phrase "to bounce therefrom to splash against the outer wall surface of the pipette" used in the present invention includes the meaning of: the case that the bounced cleaning liquid directly hits on the outer wall surface of the pipette; the case that the bounced cleaning liquid further hits on the inner circumferential surface of the concave portion, which then bounces to splash against the outer wall surface of the pipette; and the case that the bounced cleaning liquid in above two cases brings the cleaning liquid in the concave portion move, thereby letting the bounced cleaning liquid hit on the outer wall surface of the pipette via the cleaning liquid in the concave portion.

When the concave portion is formed to have an inner circumferential surface of downward tapering shape, the bouncing height of the cleaning water increases, and thus the cleaning up to the upper portion of the outer wall surface of the pipette can be readily conducted.

In particular, it is preferable that the inner circumferential surface of the concave portion is formed in substantially conical shape (circular cone, pyramidal cone, and the like), because the bouncing height of the cleaning water further increases, and because the cleaning up to the upper portion of the outer wall surface of the pipette can be readily conducted even when the velocity of the cleaning water passing through the suction and ejection portion at a tip of the pipette decreases.

When a total shape of the apparatus including the concave portion is formed in a vessel shape or preferably a vessel-shape form having a narrow opening, such as a pot, the quantity of waste of the cleaning liquid after cleaning the outer wall surface of the pipette reentering into the concave portion can be decreased.

It is preferable that the suction and ejection portion at a tip of the pipette be formed in a needle shape because the cleaning water can be swiftly ejected even if the cleaning liquid passes through the cylinder portion at a low velocity.

By forming the concave portion so as to allow the cleaning water to overflow therefrom, the outer wall surface of the pipette can be effectively cleaned with a small quantity of cleaning water, and the quantity of cleaning water remained in the concave portion can be decreased, which can prevent the contamination of the concave portion.

Specifically, it is preferable that the concave portion have a notched portion or a grove formed at upper end thereof, and/or a penetration hole formed at a side thereof because the quantity of cleaning liquid remained in the concave portion can further be decreased.

It is preferable that the suction and ejection opening of the pipette be positioned facing a position slightly shifted from the lower end of the inner circumferential surface of the concave portion because the bouncing height of the cleaning water can be further increased.

When the concave portion is formed so as the vertex of the substantially conical concave to position deviated from the center of the top opening thereof, there is further surely achieved the effect similar to that of the above-described case where the suction and ejection opening at the tip of the pipette is positioned facing a position slightly shifted from the lower end of the inner circumferential surface of the concave portion, that is, the effect of further increasing the bouncing height of the cleaning water. In particular, for an autoanalyzer which has not satisfactory positioning accuracy of the pipette, the concave portion has preferably such a form.

The method for cleaning a pipette has the steps of: positioning a pipette as the subject to be cleaned so as the suction and ejection opening of the pipette to locate in the concave portion; and bringing the cleaning liquid once passed through inside of the pipette to hit on the inner circumferential surface of the concave portion and to bounce therefrom to splash against the outer wall surface of the pipette, thereby cleaning the outer wall surface of the pipette.

When the concave portion is formed to have an inner circumferential surface of downward tapering shape, the bouncing height of the cleaning water increases, thus the cleaning up to the upper portion of the outer wall surface of the pipette can be readily conducted.

When a total shape of the apparatus including the concave portion is formed in a vessel shape or preferably a vessel shape having a narrow opening, such as a pot, it is possible to prevent the waste of cleaning liquid after cleaning the outer wall surface of the pipette from entering into the concave portion.

It is preferable that the velocity of the cleaning liquid passing through the pipette and cleaning the portion at the minimum-internal diameter be adjusted in a range from 100 to 400 cm/sec because the cleaning effect on the inner wall surface of the pipette increases with a small quantity of water.

A preferable combination of the shape of the concave portion and the velocity of cleaning liquid passing through the minimum-internal diameter portion of the pipette is that the concave portion is formed in a substantially conical shape having an inner circumferential surface of downward tapering shape, and vertex of the substantially conical concave is formed at the position deviated from the center of the top opening thereof, and that the velocity of the cleaning liquid passing through the pipette at the minimum-internal diameter portion is in a range from 100 to 400 cm/sec. With that combination, both the inner wall surface and the outer wall surface of the pipette can be simultaneously (at a time) and efficiently cleaned.

That is, the essence of the present invention is that the bounce of the cleaning liquid after passing through inside of the pipette is utilized to let the bounced cleaning water hit on the outer wall surface of the pipette to clean the outer wall surface thereof, specifically that both the inner wall surface and the outer wall surface of the pipette can be cleaned simultaneously (at a time) utilizing the bouncing of the cleaning liquid after cleaning inside of the pipette (utilizing the waste cleaning liquid). The related art, however, did not adopt the cleaning of outer wall surface of pipette utilizing the bouncing of water ejected from the pipette, and no such idea is known. Furthermore, it is not known that the same cleaning liquid is used to clean both the inner wall surface and the outer wall surface of a pipette.

According to the present invention, since the cleaning liquid passed through inside of the pipette hits on the outer wall surface of the pipette to clean the outer wall surface, there is no need of ejector of cleaning liquid for cleaning the outer wall surface of the pipette, thus the cleaning apparatus can be structured in simple design at low cost. Furthermore, the liquid which cleaned inside of a pipette is reused to clean the outer wall surface of the pipette. As a result, both the inner wall surface and the outer wall surface of a pipette can be cleaned by a single step using the same cleaning liquid, or by a single step of letting the cleaning liquid pass through inside the pipette. Therefore, the present invention provides a remarkably strong effect of shortening the pipette cleaning time and of shortening the measurement time.

Since the present invention does not clean the outer wall surface of pipette by holding the liquid which once cleaned inside of the pipette in a vessel, but cleans the outer wall surface of the pipette utilizing the bounce of cleaning liquid which passed through inside of the pipette, the capacity of the concave portion can be decreased. As a result, there is no need of discharge valve or discharge opening at the bottom of the concave portion. In addition, since the cleaning can be conducted while overflowing the cleaning liquid, the cleaning effect increases.

By forming the inner circumferential surface of the concave portion in substantially conical shape, and by letting the water eject from the pipette to a position slightly distant from the lower end of the inner circumferential surface, or by ejecting the water from the pipette into the concave portion formed so as the vertex of the substantially conical concave to position slightly deviated from the center of the opening at upper end of the concave, the bouncing height of the cleaning water can further surely be increased, thereby allowing cleaning at high portions of the pipette while decreasing the capacity of the concave portion.

DETAILED DESCRIPTION OF THE INVENTION

Figure 1:
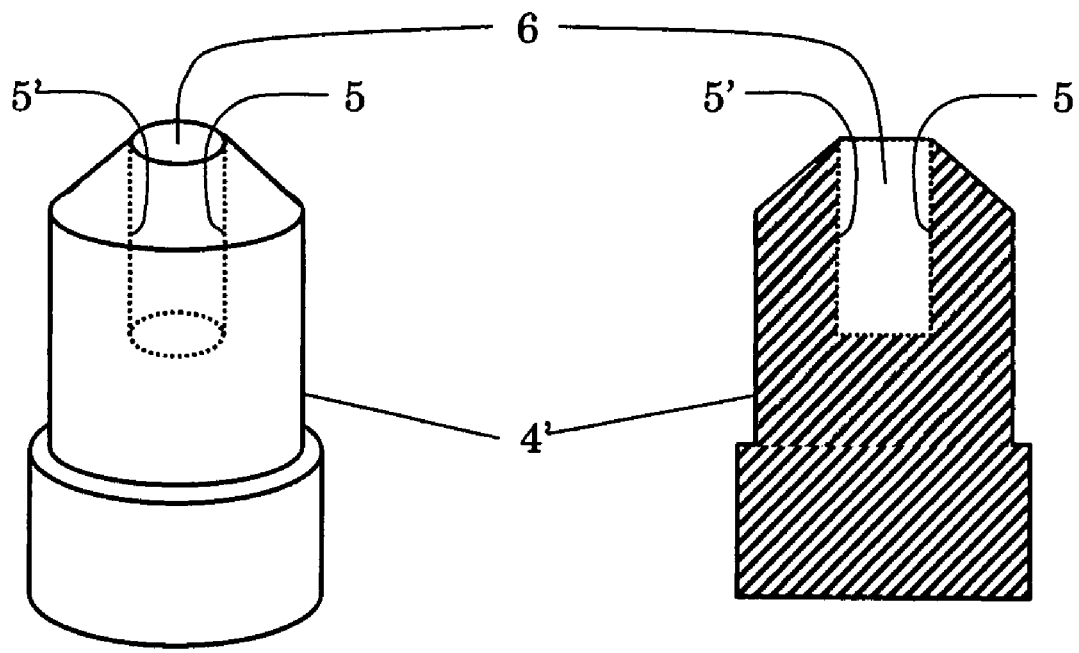
FIG. 1 shows an example of a cleaning vessel according to the present invention.

The embodiments of the present invention is described below referring to the drawings.

FIG. 1 shows an example of a cleaning vessel used in the present invention. A block is formed in substantially cylindrical shape with a top-cut conical upper portion. From the upper end of the top-cut conical portion, a concave portion having an inner circumferential surface in cylindrical shape or prism shape is formed in the substantially cylindrical body.

The cleaning water ejected from the suction and ejection opening of the pipette hits on the inner circumferential wall surface 5 of the concave portion and bounces therefrom, or further hits on the inner circumferential wall surface 5' facing the inner circumferential wall surface 5, and further bounces therefrom to hit on the outer circumferential wall surface of the pipetting needle.

Figure 2:
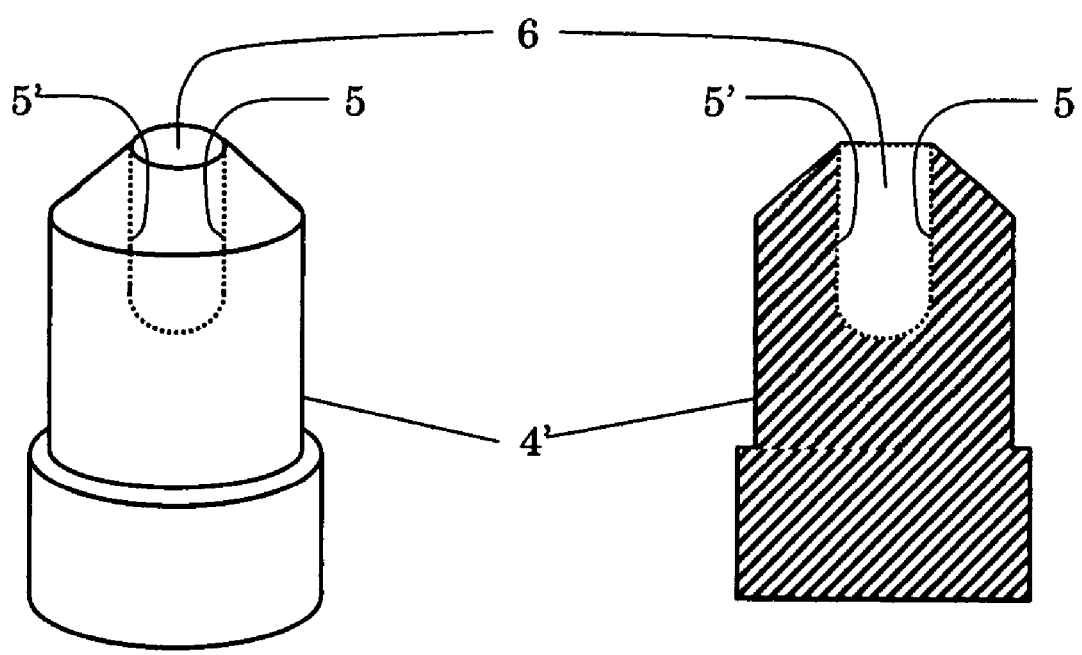
FIG. 2 shows another example of the cleaning vessel according to the present invention.

FIG. 2 shows an example of the cleaning vessel, where the bottom of the concave portion in cylindrical or prism shape is formed in a dome (hemispherical) shape. Compared with the case of flat bottom, the shape improves the bouncing of the cleaning water to some degree.

Figure 3:
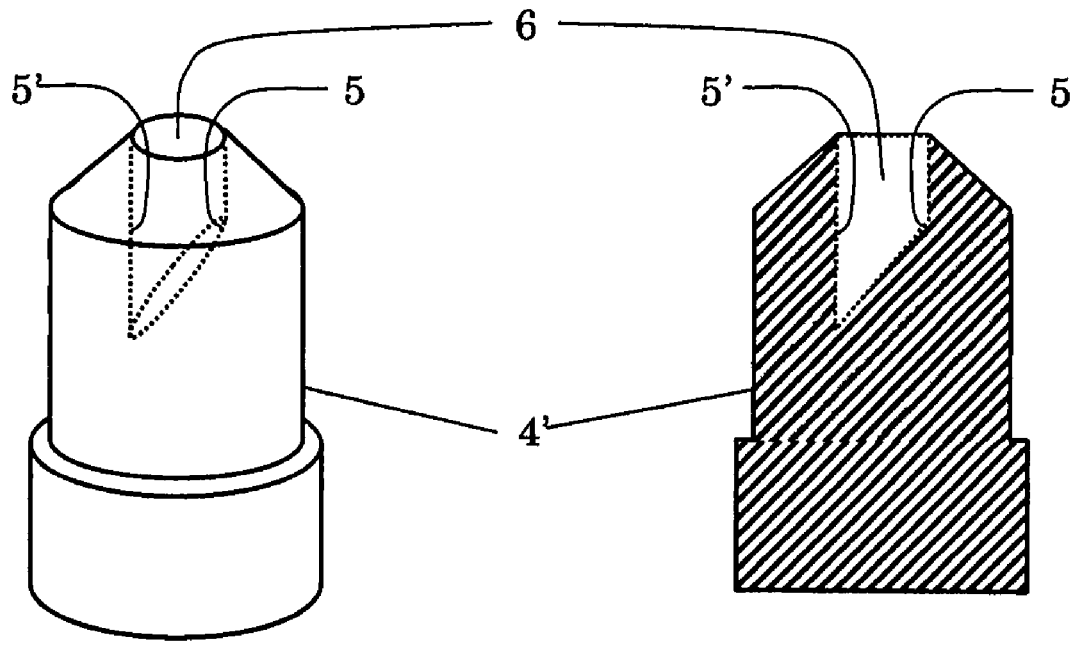
FIG. 3 shows a further example of the cleaning vessel according to the present invention.

FIG. 3 shows an example of the cleaning vessel, where the bottom of the concave portion in cylindrical or prism shape is formed in a sloped face. Compared with the case of cylindrical or prism shape of the inner circumferential surface, the shape increases the bouncing height of the cleaning water to some degree.

Figure 4:
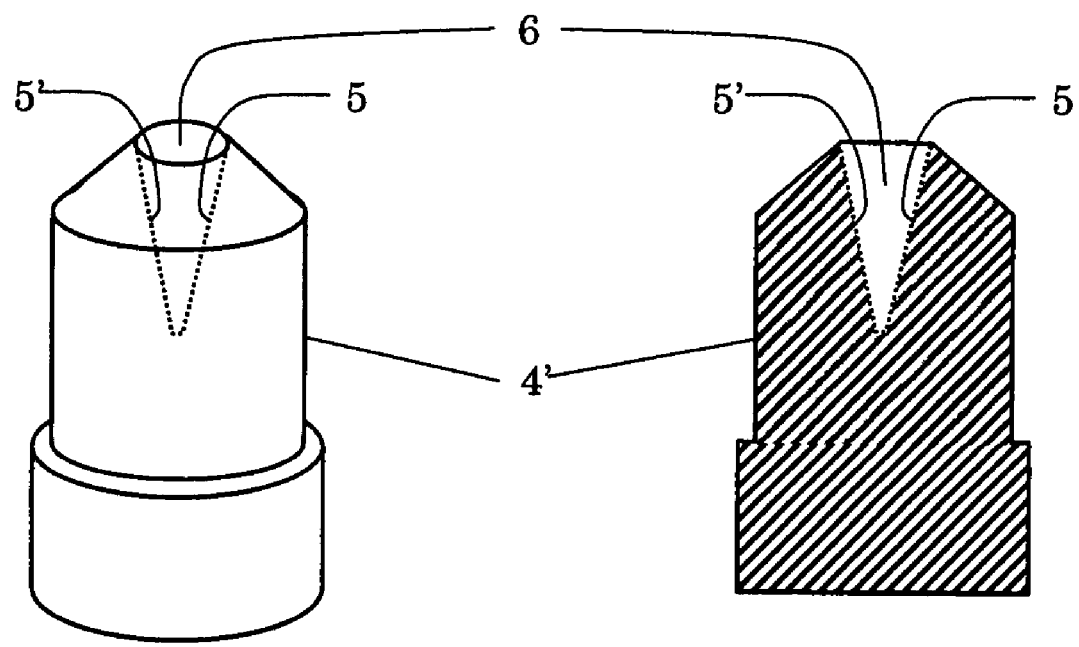
FIG. 4 shows another preferred example of the cleaning vessel according to the present invention.

FIG. 4 shows an example of the cleaning vessel, where the inner circumferential surface of the concave portion is formed in a circular cone shape. The shape further increases the bouncing height of the cleaning water, and the cleaning up to the upper portion of the outer wall surface of the pipette can be more efficiently conducted. Even if the inner circumferential surface of the concave portion is not in circular cone shape, the bouncing height of the cleaning water can be increased if only the inner circumferential surface thereof is in a shape of tapering downward, and the cleaning up to upper portion of the outer circumferential wall surface of the pipette can be efficiently performed. Nevertheless, the inner circumferential surface of the concave portion is preferably in a substantially conical shape (circular cone, pyramidal cone, and the like) with a cross section.

Figure 5:
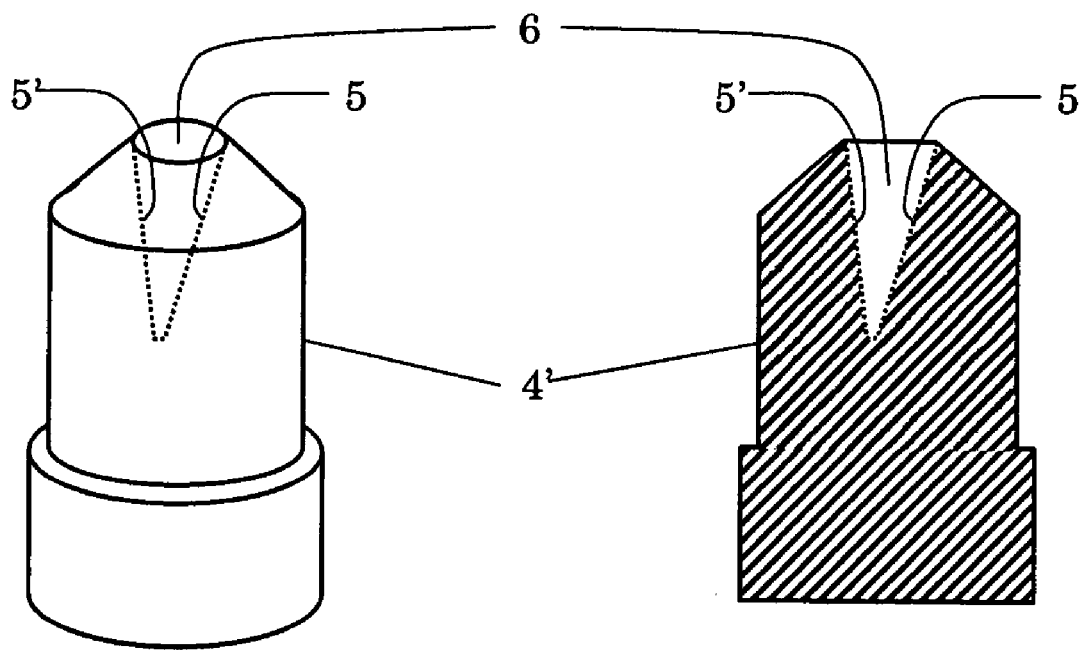
FIG. 5 shows a further preferred example of the cleaning vessel according to the present invention.

In FIG. 5, the inner circumferential surface of the concave portion is formed in substantially conical shape (circular cone, pyramidal cone, and the like) thereof being skewed by about 3°. In other words, the vertex (center) of the substantially conical shape (circular cone, pyramidal cone, and the like) is formed at a position deviated from the center of the upper opening thereof. That is, the surface 5 on which the cleaning liquid ejected from the suction and ejection opening of the pipette hits has a smaller tilt angle than that of the surface 5' on which the bounced cleaning liquid hits. With that configuration, the height of the bounced (splashed) cleaning liquid can be further surely increased. Consequently, it is preferable that the inner circumferential surface of the concave portion have a smaller slope of the surface 5 on which the cleaning liquid ejected from the suction and ejection opening of the pipette hits than the slope of the surface 5' on which the bounced cleaning liquid hits. By forming the inner circumferential surface in a slightly skewed cone shape, the bouncing height can be increased even when the cleaning liquid ejected from the suction and ejection opening of the pipette hits on the center or near-center of the circular cone.

Figure 6:
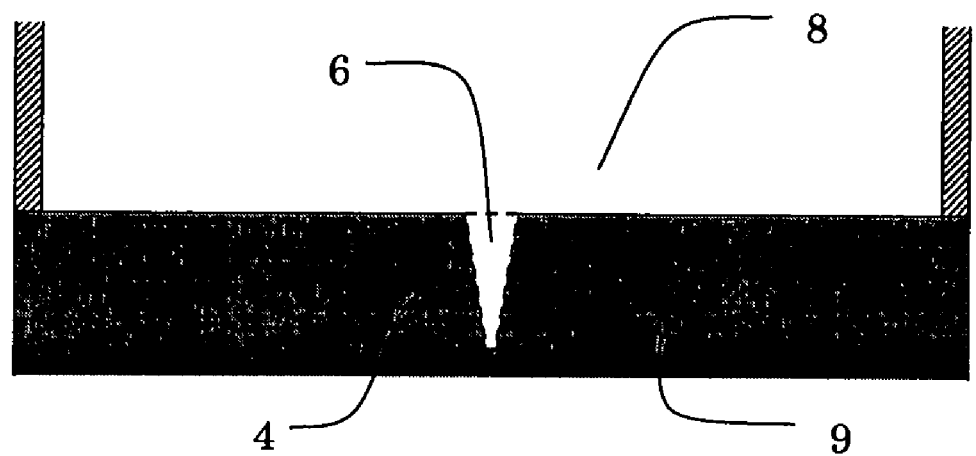
FIG. 6 shows still another example of the cleaning vessel according to the present invention.

FIG. 6 is a schematic drawing illustrating the pipette cleaning portion 8 in an apparatus having the concave portion 4 formed. The FIG. 6 shows an example of forming a conical shape concave portion 4 at the bottom 9 of the pipette cleaning portion 8.

Figure 7:
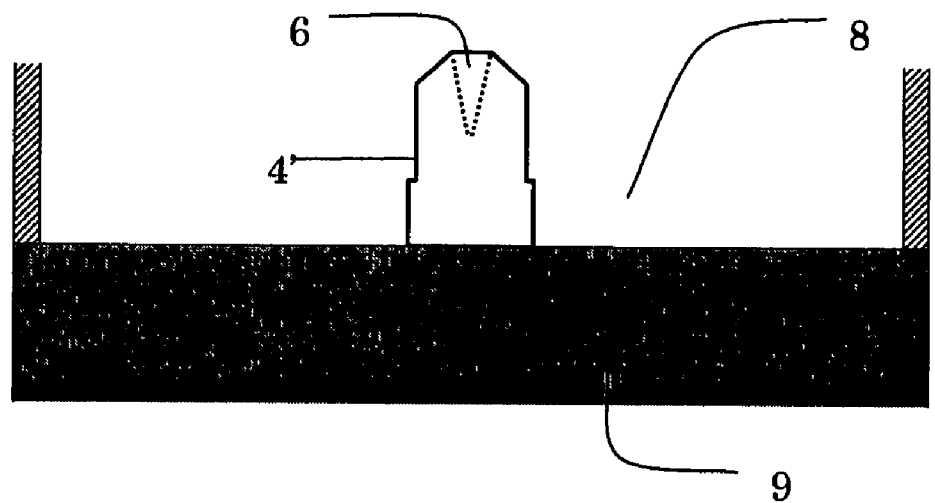
FIG. 7 shows an example of a concave portion according to the present invention.

FIG. 7 shows an example which has a block-shape cleaning vessel 4' having the concave portion 4 on the upper surface of bottom 9 of the pipette cleaning portion 8 in the apparatus. As in the example, it is preferable that a so-called pot-shape (narrow opening) cleaning vessel 4' having the concave portion 4 is erected on the upper surface of bottom 9 of the cleaning portion because the quantity of re-entering waste cleaning liquid after cleaned the outer wall surface of the pipette into the concave portion can be decreased.

For above-examples, the concave portion is formed to allow the cleaning liquid to always overflow therefrom during cleaning. Since therefore the cleaning liquids on the inner wall surface and on the outer wall surface are always replaced with a cleaning liquid with small contamination, the cleaning effect can be attained. The capacity of the concave portion is preferably in a range from 1/20 to 1/5 times the total amount of the cleaning liquid per single cleaning cycle, more preferably from 1/15 to 1/8 times, and further preferably about 1/10 times. According to the present invention, the cleaning liquid keeps moving so that the cleaning liquid overflows from the opening 6 even with a quantity smaller than the capacity of the concave portion.

Figure 8:
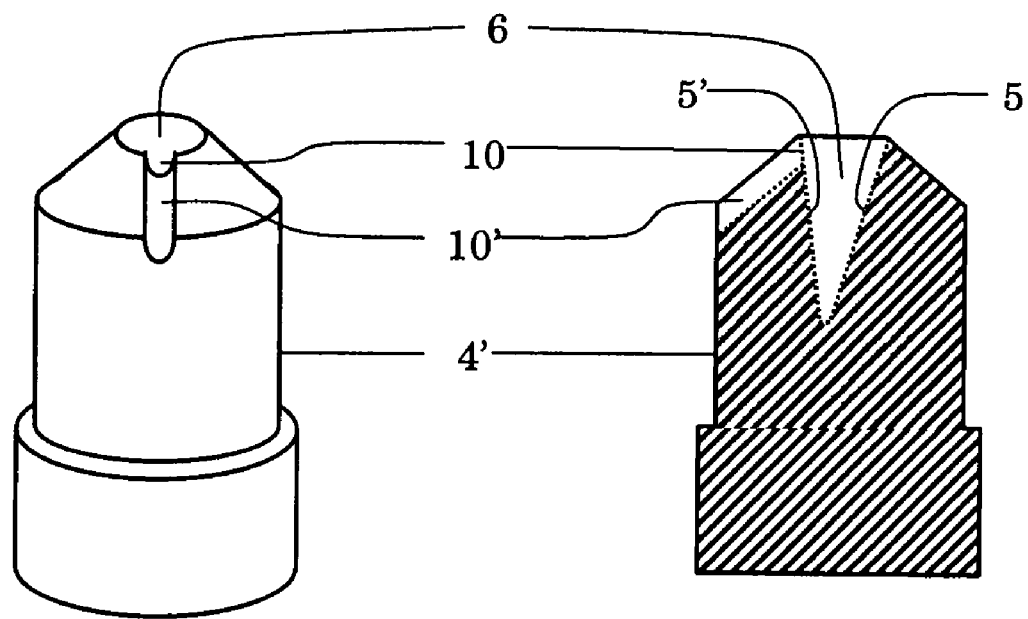
FIG. 8 shows a still further preferred example of the cleaning vessel according to the present invention.

In the example given in FIG. 8, there are a notch 10 and a groove 10' formed at upper end of the opening 6 of the concave portion. With the configuration, the quantity of cleaning liquid remained in the concave portion can further be decreased, which can decrease the quantity of cleaning liquid remained in the concave portion, thus making the overflow easy. Instead of forming the groove at upper end, a penetration hole may be formed at a side of the upper portion. Alternatively, the groove is not formed, and only a notch may be formed. Furthermore, the notch formed from upper end may be replaced with a penetration hole formed at the upper portion.

In this manner, with the aim to allow overflowing the cleaning liquid, further by forming a groove, a notch portion, or a penetration hole, the quantity of cleaning liquid remained in the concave portion decreases, thereby decreasing the quantity of cleaning water remained in the concave portion, and also decreasing the capacity of the concave portion. Consequently, the cleaning water in the concave portion becomes easily replacing with fresh cleaning water, and there is no need of installing a discharge valve at bottom of the concave portion.

Next, the cleaning method according to the present invention is described below referring to FIGS. 9 to 11.

Figure 9:
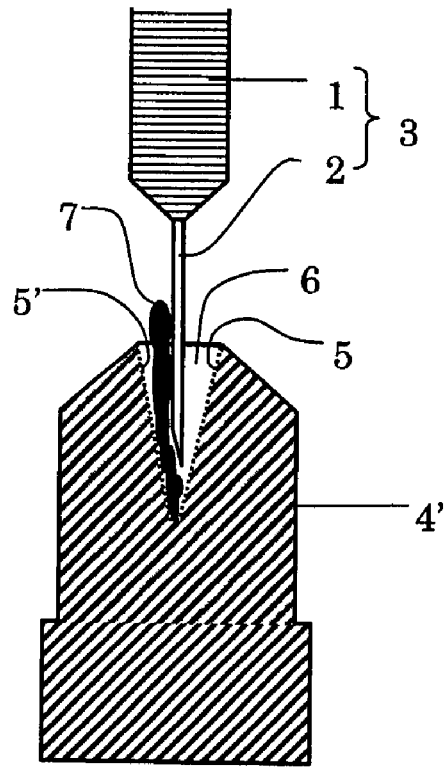
FIG. 9 shows a cross-sectional view of an example of the present invention.

As illustrated in FIG. 9, a probe (pipette) 3 has a pipette body (pipette cylinder) 1 in cylindrical shape and a pipetting needle 2, having a suction and ejection opening on its tip and connected to the lower end of the pipette body 1. The probe (pipette) 3 is located in a concave portion 4 in substantially circular cone shape.

The cleaning liquid ejected from the suction and ejection opening at the tip of the pipetting needle 2 hits on the inner circumferential wall surface 5 of the concave portion and then bounces therefrom to hit on the facing inner circumferential wall surface 5' opposed to the surface 5, further then bounces therefrom to hit on the outer circumferential wall surface of the pipetting needle 2.

Figure 10:
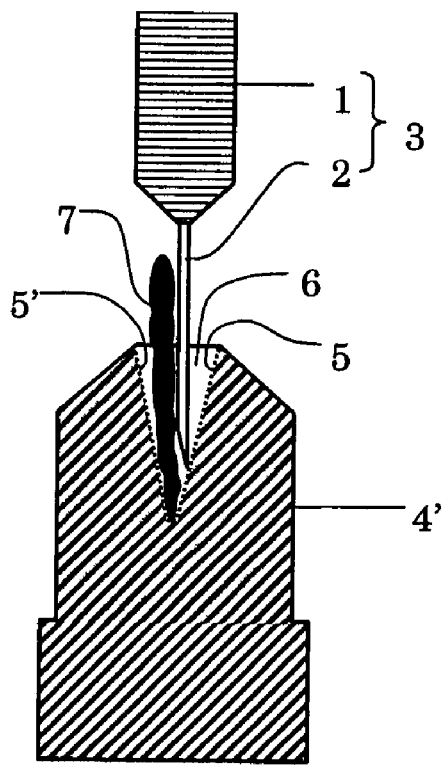
FIG. 10 shows a cross-sectional view of another example of the present invention.

As illustrated in FIG. 10, when the suction and ejection opening at the tip of the pipetting needle is located to face a position slightly deviated from the lowest end in the inner circumferential surface, and when the cleaning liquid 7 ejected from the suction and ejection opening at the tip of the pipetting needle 2 is brought not to directly hit on the vertex (center: lowest end of the inner circumferential surface) of the circular cone (or brought to eject onto the inner circumferential surface), then, compared with the case of FIG. 9 where the cleaning liquid 7 ejected from the suction and ejection opening at the tip of the pipetting needle 2 hits on the vertex (center: lowest end of the inner circumferential surface) of the circular cone the configuration is preferable because the bouncing height can be increased.

Figure 11:
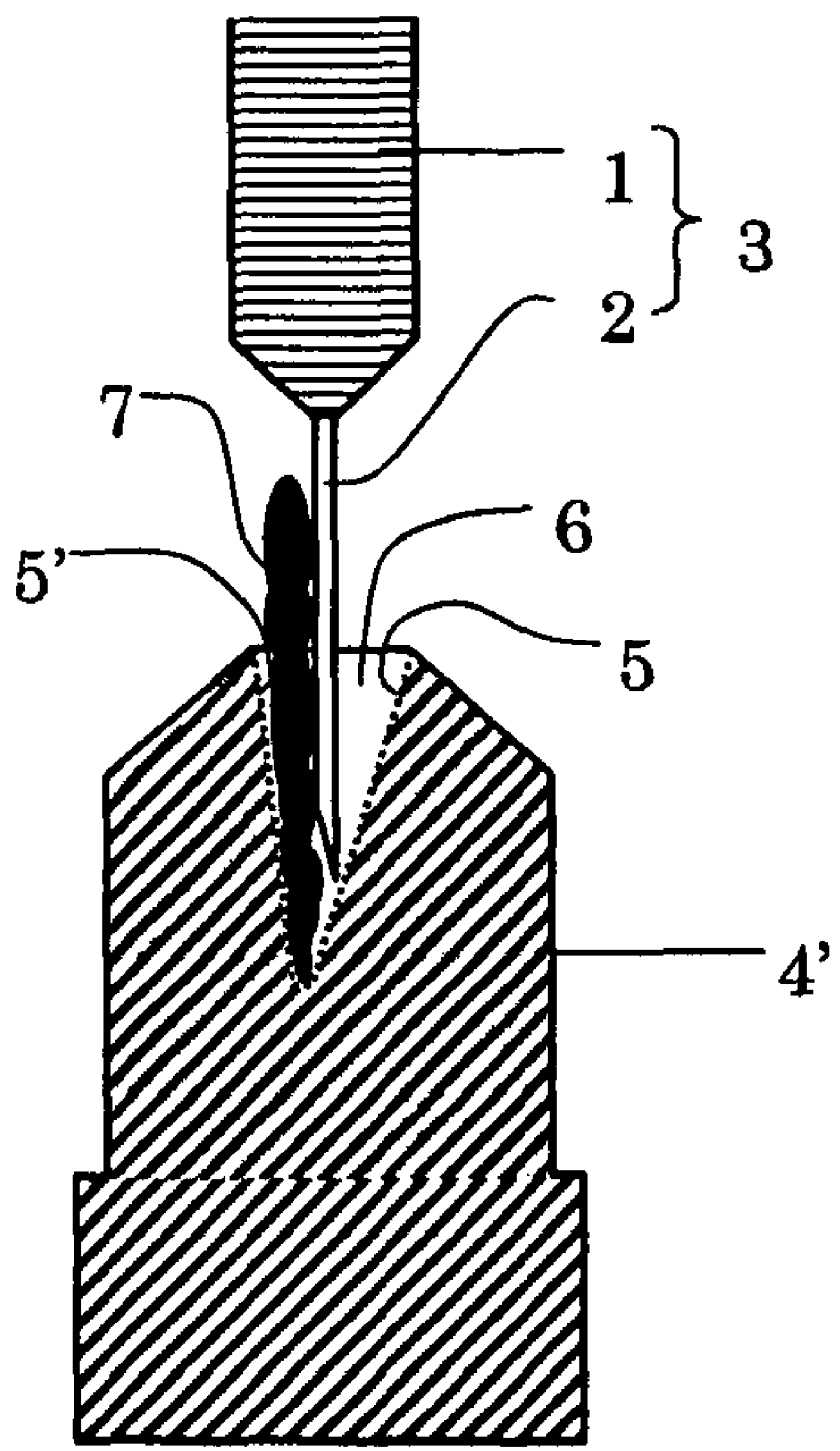
FIG. 11 shows a cross-sectional view of further example of the present invention.

FIG. 11 shows a case in which the applied concave portion has a shape of circular cone skewed by 3°, i.e. the applied concave portion is formed so as the vertex (center) of the circular cone is deviated from the center of the top opening. Forming the concave portion in a shape of slightly skewed inner circumferential surface (cone) is preferred because the bouncing height can be increased even when the cleaning liquid ejected from the suction and ejection opening at the tip of the pipetting needle 2 hits on the center or near-center of the circular cone.

In general apparatuses, care shall be paid on applying the method given in FIG. 10 where the suction and ejection opening at the tip of the pipetting needle is located facing a position slightly shifted from the lowest end of the inner circumferential surface. That is, since the accuracy of pipette positioning in general apparatuses is not so high, it is difficult in some cases to keep the pipette position at a position deviated from the lowest end of the inner circumferential surface, (in some cases, the pipette becomes deviated or not-deviated). Therefore, when a concave portion which is formed so as the vertex (center) of the circular cone shown in FIG. 11 to locate at a position deviated from the center of the top opening, the bouncing height of the cleaning water can further simply and surely be increased.

To increase the bouncing height of the cleaning liquid hitting on the inner circumferential surface of the concave portion, the cleaning water is required to be swiftly ejected from the suction and ejection opening at the tip of the pipette. When, however, the cleaning effect on the inner surface of the pipette cylinder 1 and the inner surface of the pipetting needle 2 is considered, the velocity of cleaning water passing through the cylinder portion 1 and the pipetting needle 2 cannot be increased to a very high level. If the velocity thereof is excessively high, the water in the vicinity of the inner wall surface stops flowing, although the water at center portion in the cylinder and at center portion in the pipetting needle flows as a laminar flow, which fails to attain sufficient cleaning effect with a limited specified quantity of water. Consequently, to increase the bouncing height even when the cleaning liquid passes through the cylinder portion 1 and the pipetting needle 2 at a small velocity, it is more preferable for the inner circumferential surface of the concave portion to have a shape of tapering downward as described above, and most preferable therefor is to have a shape of substantially conical shape (circular cone, pyramidal cone, and the like).

The velocity of the cleaning liquid passing through the minimum-internal diameter portion of the pipette, (for example, the pipetting needle), is arbitrary if only the velocity allows cleaning the outer wall surface of the pipette utilizing the bounce of the cleaning liquid after passed through inside of the pipette, and examples of the velocity are in a range from 100 to 800 cm/sec, and preferably from 100 to 600 cm/sec. Among these velocities, specifically preferred ones are from 100 to 400 cm/sec as the velocity of cleaning liquid passing through the minimum-internal diameter portion (for example, the pipetting needle) of the pipette because a small quantity of water increases the cleaning effect on the inner wall surface of the pipette and increases the bouncing height of the cleaning liquid, thus allowing cleaning of the outer circumferential wall surface of the pipette, i.e. because both the inner wall surface and the outer wall surface of the same pipette can be cleaned in a single step (with the same cleaning liquid), and further preferred ones are from 100 to 200 cm/sec, and most preferred ones are about 150 cm/sec.

When the velocity of cleaning liquid passing through the minimum-internal diameter portion in the pipette is within the above range, the velocity of cleaning liquid passing through the portion having larger internal diameter than the minimum internal diameter of the pipette (for example, cylinder) naturally becomes smaller. Therefore, the velocity of cleaning liquid passing through the portion having larger internal diameter than the minimum internal diameter of the pipette (for example, cylinder) may be arbitrarily selected so as the velocity of cleaning liquid flowing through the portion having the minimum internal diameter of the pipette to become within the above range, preferably in a range from 5.0 to 20 cm/sec, more preferably from 5.0 to 15 cm/sec, and most preferably about 10 cm/sec.

The present invention includes the case that the inside (inner wall surface) of the pipette is firstly cleaned, and then the outer wall surface of the pipette is cleaned. However, the velocity of the cleaning liquid at the time of cleaning the outer wall surface of the pipette is not necessarily limited to the above range. That is, firstly the cleaning liquid is brought to pass through inside of the pipetting needle at a velocity not establishing laminar flow (for example, in above range) to clean the inside (inner wall surface) of the pipette, and then the velocity of the cleaning liquid is increased to swiftly eject thereof from the suction and ejection opening of the pipette, thus to clean the outer wall surface of the pipette using the cleaning liquid which hit on and bounced from the inner circumferential surface of the concave portion.

In the above examples, the pipetting needle 2 having a suction and ejection opening at the tip thereof is connected to the lower end of the cylindrical pipette body (pipette cylinder) 1. By forming the suction and ejection portion at the tip of the pipette in a needle shape, the cleaning liquid can be swiftly ejected from the suction and ejection opening even when the cleaning liquid passes through the cylinder portion 1 at a small velocity, and the bouncing height of the cleaning liquid can be increased to perform cleaning of the outer circumferential surface of the pipette without trouble.

In general, the contaminated portion on the outer wall surface of the pipette ranges from a height half or less of the total length of the pipetting needle 2 to the lower end thereof. Accordingly, the cleaning water is required to bounce only to a height of about half the total length of the pipetting needle.

According to the present invention, the cleaning water after passed through inside of the pipette hits on the inner wall surface of the concave portion, and the bounced water is used to clean the outer wall surface of the pipette. Consequently, there is no need of a special apparatus to eject the cleaning water for cleaning the outer wall surface of the pipette.

Furthermore, since both the inner wall surface and the outer wall surface of a pipette are cleaned in a single step, the cleaning time is decreased, thereby attaining advantage of shortening the measurement time.

The invention claimed is:

1. A combination of a pipette and a pipette cleaning apparatus, comprising:
    the pipette comprising a pipetting needle including a suction and ejection opening at a tip thereof; and
    the cleaning apparatus comprising a concave portion including a cavity, said cavity being internally bounded by an inner circumferential surface extending from a top opening to a lower end of the cavity, said cavity being configured to receive said pipetting needle of the pipette positioned therein for cleaning of the pipette, said pipetting needle and said cavity being mutually dimensioned so that pipetting needle is receivable within the cavity with the tip positioned proximate to said lower end such that a cleaning liquid passed through an inside of the pipette and ejected from the tip strikes the inner circumferential surface of the cavity and bounces therefrom to splash against an outer wall surface of the pipetting needle over a sufficient length thereof to effectively clean the outer wall surface, said inner circumferential surface presenting a continuously downward tapering configuration from said top opening to said lower end of the cavity.

2. The combination according to claim 1, wherein the inner circumferential surface of the cavity is formed in a substantially conical shape.

3. The combination according to claim 1 or 2, wherein a total shape of the apparatus including the concave portion is in a form of a vessel.

4. The combination according to claim 1 or 2, wherein the cavity is adapted to receive at least a portion of a suction and ejection portion of the pipette at a tip of the pipette formed in a needle shape.

5. The combination according to claim 1 or 2, wherein the concave portion is formed to allow the cleaning liquid to overflow from said cavity.

6. The combination according to claim 5, wherein the concave portion includes a notched portion or a groove formed at an upper end thereof, and/or a penetration hole formed at a side thereof, communicative with said cavity, so as to facilitate outflow of the cleaning liquid from the cavity such that a quantity of the cleaning liquid remaining in the cavity decreases.

7. The combination according to claim 1, wherein the cavity is configured to have a suction and ejection opening of the pipette positioned facing a position slightly shifted from the lower end of the cavity.

8. A pipette cleaning apparatus, comprising:
a concave portion including a substantially conical cavity arranged along a conical axis, said cavity being internally bounded by an inner circumferential surface extending from a top opening to a lower end of the cavity, said cavity being configured-to receive a pipetting needle of a pipette positioned therein for cleaning of the pipette, such that a cleaning liquid passed through an inside of the pipette and ejected from a tip of the pipetting needle strikes the inner circumferential surface of the cavity and bounces therefrom to splash against an outer wall surface of the pipetting needle, thereby cleaning the outer wall surface, said inner circumferential surface presenting a downward tapering configuration from said top opening to said lower end of the cavity at which the substantially conical cavity terminates at a vertex, said vertex of the substantially conical cavity being formed at a position which is horizontally offset from a center of said top opening thereof.

9. A method for cleaning a pipette including a pipetting needle, comprising:
positioning the pipetting needle to be cleaned so that a suction and ejection opening thereof is located in a cavity provided in a concave portion of a pipette cleaning apparatus, said cavity being internally bounded by an inner circumferential surface extending from a top opening to a lower end of said cavity, said inner circumferential surface presenting a downward tapering configuration from said top opening to said lower end of the cavity; and
causing a cleaning liquid to strike an inner circumferential surface of the cavity and to bounce therefrom to splash against an outer wall surface of the pipette by passing the cleaning liquid through an inside of the pipette, so as to effect cleaning of the outer wall surface of the pipetting needle.

10. The method for cleaning a pipette according to claim 9, wherein a total shape of the apparatus including the concave portion is in a form of a vessel.

11. The method for cleaning a pipette according to claim 9, wherein a velocity of the cleaning liquid passing through the pipette at a minimum-internal diameter portion of the pipette is in a range from 100 to 400 cm/sec.

12. The method for cleaning a pipette according to claim 9, wherein:
the cavity is formed as a substantially conical cavity arranged along a conical axis;
a vertex of the substantially conical cavity is formed at a position which is horizontally offset from a center of said top opening thereof; and
the velocity of the cleaning liquid passing through the pipette at a minimum-internal diameter portion is in a range from 100 to 400 cm/sec.

13. The method for cleaning a pipette according to claim 9, wherein the inner circumferential surface of the cavity is formed in a substantially conical shape.

14. The method for cleaning a pipette according to claim 9, wherein the pipette to be cleaned is positioned so that the suction and ejection opening of the pipette is located to face a position slightly shifted from the lower end of the cavity.

15. The method for cleaning a pipette according to claim 13, wherein a vertex of the substantially conical cavity is formed at a position which is horizontally offset from a center of said top opening thereof.

16. A combination of a pipette and a pipette cleaning apparatus, comprising:
the pipette comprising a pipetting needle including a suction and ejection opening at a tip thereof; and
the cleaning apparatus comprising a concave portion including a cavity, said cavity being internally bounded by an inner circumferential. surface extending from a top opening to a lower end of the cavity, said cavity being configured to receive said pipetting needle of the pipette positioned therein for cleaning of the pipette, said pipetting needle and said cavity being mutually dimensioned so that pipetting needle is receivable within the cavity with the tip positioned proximate to said lower end such that a cleaning liquid passed through an inside of the pipette and ejected from the tip strikes the inner circumferential surface of the cavity and bounces therefrom to splash against an outer wall surface of the pipetting needle over a sufficient length thereof to effectively clean the outer wall surface, at least a portion of said inner circumferential surface presenting a sloped face continuously extending downwardly from an uppermost position at said top opening or below said top opening to said lower end of the cavity such that said cavity is downwardly tapered at least in a region thereof corresponding to said sloped face.

17. The combination according to claim 16, wherein a total shape of the pipette cleaning apparatus including the concave portion is in a form of a vessel.

18. A method for cleaning the pipette using the pipette cleaning apparatus of the combination according to claim 16, comprising:
positioning the pipette to be cleaned so that the suction and ejection opening thereof is located in said cavity provided in concave portion of the pipette cleaning apparatus below said uppermost position; and
causing a cleaning liquid to strike an inner circumferential surface of the cavity and to bounce therefrom to splash against an outer wall surface of the pipette by passing the cleaning liquid through an inside of the pipette, so as to effect cleaning of the outer wall surface of the pipetting needle.

19. The method for cleaning a pipette according to claim 18, wherein the pipette to be cleaned is positioned so that the suction and ejection opening of the pipetting needle is located to face a position slightly shifted from the lower end of the cavity.

* * * * *